(12) United States Patent
Wang et al.

(10) Patent No.: US 7,875,736 B2
(45) Date of Patent: Jan. 25, 2011

(54) INTERMEDIATE COMPOUNDS AND PROCESSES FOR THE PREPARATION OF 7-BENZYLOXY-3-(4-METHOXYPHENYL)-2H-1-BENZOPYRAN

(75) Inventors: Eng-Chi Wang, Kaohsiung (TW); Sie-Rong Li, Taipei County (TW)

(73) Assignee: KaoHsiung Medical University, Taipei (TW)

( * ) Notice: Subject to any disclaimer, the term of this patent is extended or adjusted under 35 U.S.C. 154(b) by 0 days.

(21) Appl. No.: 12/468,712

(22) Filed: May 19, 2009

(65) Prior Publication Data
US 2010/0298582 A1 Nov. 25, 2010

(51) Int. Cl.
C07D 311/50 (2006.01)
C07C 49/213 (2006.01)
C07C 43/215 (2006.01)
(52) U.S. Cl. ........................ 549/406; 568/325; 568/646
(58) Field of Classification Search ................. 568/325, 568/646; 549/406
See application file for complete search history.

(56) References Cited

U.S. PATENT DOCUMENTS

2007/0027329 A1 2/2007 Setchell et al.
2007/0149788 A1 6/2007 Hyatt

FOREIGN PATENT DOCUMENTS

WO WO 00/49009 8/2000
WO WO 2005/103025 11/2005

OTHER PUBLICATIONS

Li et al, Tet. Letters, vol. 50, p. 2121-2123, May 5, 2009.*
Kenneth H. Dudley et al., "Flavonoids. IV. A novel Clemmensen reduction. The direct conversion of 2-alkylisoflavones to 2-alkyl-3-isoflavenes", J. Org. Chem., 1967, 32 (7), pp. 2317-2321.
S. Ramadas et al., "Enantioselective acylation of 2-hydroxymethyl-2,3-dihydrobenzofurans catalysed by lipase from Pseudomonas cepacia (Amano PS) and total stereoselective synthesis of (−)-(R)-MEM-protected arthrographol", Tetrahedron: Asymmetry 11 (2000) pp. 3375-3393.
Veselin Maslak et al., "Design, Synthesis, and Conformational Dynamics of a Gated Molecular Basket", J. Am. Chem. Soc., 2006, 128, pp. 5887-5894.
Rajeev S. Muthyala et al., "Equol, a natural estrogenic metabolite from soy isoflavones: convenient preparation and resolution of R- and S-equols and their differing binding and biological activity through estrogen receptors alpha and beta" Bioorganic & Medicinal Chemistry 12 (2004), pp. 1559-1567.
Santosh J. Gharpure et al., "o-Quinone methide based approach to isoflavans: application to the total syntheses of equol, 3'-hydroxyequol and vestitol" Tetrahedron Letters 49 (2008) pp. 2974-2978.
Jennifer M. Heemstra et al., "Total Synthesis of (S)-Equol" Organic Letters, 2006, vol. 8, No. 24, pp. 5441-5443.

Yu-Chen Chang et al., "Microwave-Mediated Synthesis of Anticarcinogenic Isoflavones from Soybeans" J. Agric. Food Chem., 1994, 42, pp. 1869-1871.
Yuji Takashima et al., "New Synthetic route to (S)-(—)-equol through allylic substitution" Tetrahedron Letters 49 (2008) pp. 5156-5158.
Guan-Yeow Yeap et al., "Synthesis and mesomorphic properties of 7-acyloxy-3-(4-acyloxyphenyl)-4H-1-benzopyran-4-one" Liquid Crystals, vol. 34, No. 5, (2007), pp. 649-654.
Sang-Hun Jung et al., "Structural requirement of isoflavonones for the inhibitory activity of interleukin-5" European Journal of Medicinal Chemistry 38 (2003) pp. 537-545.
Himanshu Singh et al., "A convenient one-pot synthesis of 7-hydroxy-isoflavones from resorcinol with substituted phenylacetic acids", Tetrahendron Letters 47 (2006) pp. 8161-8163.
Francois-Xavier Felpin et al., "Practical and efficient entry to isoflavones by Pd(0)/C-mediated Suzuki-Miyaura reaction. Total synthesis of geranylated isoflavones", Tetrahedron 63 (2007) pp. 3010-3016.
Michael Seeger et al., "Biotransformation of Natural and Synthetic Isofavonoids by Two Recombinant Microbial Enzymes", Applied and Environmental Microbiology, (2003), vol. 69, No. 9, pp. 5045-5050.
Maria Luczkiewicz et al., "Co-cultures of shoots and hairy roots of Genista tinctoria L. for synthesis and biotransformation of large amounts of phytoestrogens" Plant Science 169 (2005) pp. 862-871.
M. Miyazawa et al., "Biotransformation of isoflavones by Aspergillus niger, as biocatalyst".J. of Molecular Catalysis B: Enzymatic 27 (2004) pp. 91-95.

(Continued)

*Primary Examiner*—Bernard Dentz
(74) *Attorney, Agent, or Firm*—Fish & Richardson P.C.

(57) ABSTRACT

Disclosed herein is a compound of formula (I):

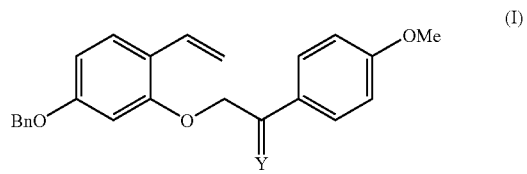

wherein:
  Bn represents benzyl;
  Me represents methyl; and
  Y represents an oxygen atom or a $CH_2$ group.

The compound of formula (I) can be used in the preparation of 7-benzyloxy-3-(4-methoxyphenyl)-2H-1-benzopyran, Preparation processes of said compound of formula (I) are also disclosed herein.

10 Claims, No Drawings

OTHER PUBLICATIONS

Paige R. Brooks et al., "Boron Trichloride/Tetra-*n*-Butylammonium Iodide: A Mild, Selective Combination Reagent for the Cleavage of Primary Alkyl Aryl Ethers" J. Org. Chem., vol. 64, No. 26, (1999), pp. 9719-9721.

Sie-Rong Li., et al., "Synthesis of haginin E. equol, daidzein, and formononetin from resorcinol via an isoflavene intermediate", Tetrahedron Letter 50 (2009) 2121-2123.

* cited by examiner

INTERMEDIATE COMPOUNDS AND PROCESSES FOR THE PREPARATION OF 7-BENZYLOXY-3-(4-METHOXYPHENYL)-2H-1-BENZOPYRAN

BACKGROUND OF THE INVENTION

1. Field of the Invention

This invention relates to intermediate compounds and processes for the preparation of 7-benzyloxy-3-(4-methoxyphenyl)-2H-1-benzopyran.

2. Description of the Related Art

In *J. Org. Chem.* (1967), 32:2317-2321, K. H. Dudley et al, reported an approach to synthesize 7-benzyloxy-3-(4-methoxyphenyl)-2H-1-benzopyran (also called 7-benzyloxy-4'-methoxy-$\Delta^3$-isoflavene), which started from 7-hydroxy-4'-methoxy-isoflavone (also called formononetin) and involved the formation of two intermediate compounds, i.e., 7-benzyloxy-4'-methoxyisoflavone and 7-benzyloxy-4'-methoxyisoflavanol. However, said approach is complicated in practice and affords a yield that is not satisfactory.

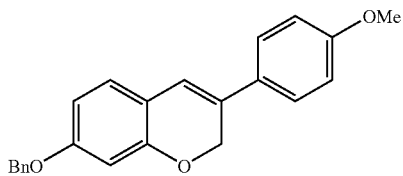

(7-benzyloxy-4'-methoxy-$\Delta^3$-isoflavene, in which Bn represents benzyl and Me represent methyl).

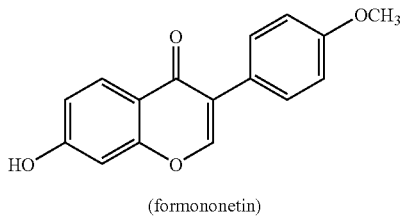

(formononetin)

Accordingly, there is a need to develop a process that is simple and efficient in the preparation of 7-benzyloxy-3-(4-methoxyphenyl)-2H-1-benzopyran while affording a satisfactorily high yield.

SUMMARY OF THE INVENTION

Therefore, according to a first aspect, this invention provides a compound of formula (I):

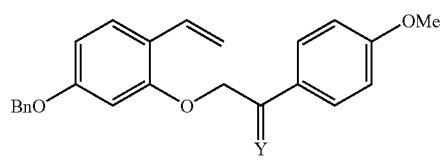

wherein:
Bn represents benzyl;
Me represents methyl; and
Y represents an oxygen atom or a $CH_2$ group.

In a second aspect, this invention provides a process for preparing 7-benzyloxy-3-(4-methoxyphenyl)-2H-1-benzopyran, comprising subjecting a compound of formula (I) as described above, wherein Y is a $CH_2$ group, to a ring closing metathesis reaction in the presence of a catalyst.

In a third aspect, this invention provides a process for preparing 4-benzyloxy-2-[2-(4-methoxyphenyl)allyloxy]-1-vinylbenzene, comprising reacting 2-(5-benzyloxy-2-vinylphenoxy)-1-(4-methoxyphenyl)ethanone with a mixture of methyl triphenyl phosphonium bromide and a first base.

In a fourth aspect, this invention provides a process for preparing 2-(5-benzyloxy-2-vinylphenoxy)-1-(4-methoxyphenyl)ethanone, comprising reacting 4-benzyloxy-2-hydroxybenzaldehyde with a mixture of methyl triphenyl phosphonium bromide and a second base, followed by reaction with 2-bromo-4'-methoxyacetophenone.

DETAILED DESCRIPTION OF THE INVENTION

For the purpose of this specification, it will be clearly understood that the word "comprising" means "including but not limited to", and that the word "comprises" has a corresponding meaning.

It is to be understood that, if any prior art publication is referred to herein, such reference does not constitute an admission that the publication forms a part of the common general knowledge in the art, in Taiwan or any other country.

Unless defined otherwise, all technical and scientific terms used herein have the meaning commonly understood by a person skilled in the art to which this invention belongs. One skilled in the art will recognize many methods and materials similar or equivalent to those described herein, which could be used in the practice of the present invention. Indeed, the present invention is in no way limited to the methods and materials described. For clarity, the following definitions are used herein.

In this invention, the applicants endeavored to develop a new strategy for the synthesis of 7-benzyloxy-3(4-methoxyphenyl)-2H-1-benzopyran that can be started from a simple compound and works efficiently to afford a high yield of the desired product.

Accordingly, this invention provides a compound of formula (I):

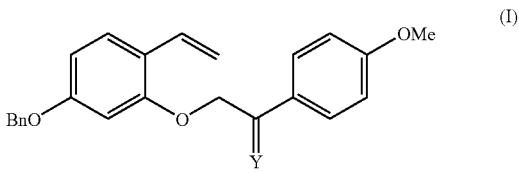

wherein:
Bn represents benzyl;
Me represents methyl; and
Y represents an oxygen atom or a $CH_2$ group.

The applicants found that 7-benzyloxy-3-(4-methoxyphenyl)-2H-1-benzopyran can be easily synthesized from a compound of formula (I) as described above, wherein Y is a $CH_2$ group, through a ring closing metathesis reaction in the presence of a catalyst.

The catalyst suitable for use in this invention in the synthesis of 7-benzyloxy-3-(4-methoxyphenyl)-2H-1-benzopyran includes, but is not limited to: Grubbs' catalyst (II), Hoveyda- Grubbs' catalyst, and Grubbs' catalyst (I). In a preferred embodiment of this invention, the catalyst is Grubbs' catalyst (II).

According to this invention, the ring closing metathesis reaction may be carried out in the presence of an appropriate solvent, including, but not limited to: $CH_2Cl_2$, benzene, and toluene. In a preferred embodiment of this invention, the ring closing metathesis reaction may be carried out in the presence of $CH_2Cl_2$.

The applicants found that the compound of formula (I) as described above, wherein Y is a $CH_2$ group, can be easily synthesized by reacting 2-(5-benzyloxy-2-vinylphenoxy)-1-(4-methoxyphenyl)ethanone with a mixture of methyl triphenyl phosphonium bromide and a first base.

The first base suitable for use in this invention includes, but is not limited to: potassium tert-butoxide (t-BuOK), sodium tert-butoxide (t-BuONa), n-butyllithium (n-BuLi), phenyllithium (PhLi), tert-butyllithium (t-BuLi), sodium hydride (NaH), sodium hexamethyldisilazide (NaHMDS), potassium hexamethyldisilazide (KHMDS), triethylamine ($Et_3N$), and sodium methoxide. In a preferred embodiment of this invention, the first base is t-BuOK.

The synthesis of the compound of formula (I) as described above, wherein Y is a $CH_2$ group, may be carried out in the presence of an appropriate solvent, including, but not being limited to: tetrahydrofuran (THF), diethyl ether ($Et_2O$), tetrahydropyran (THP), N,N-dimethylformamide (DMF), dimethyl sulfoxide (DMSO), dimethoxyethane (DME), and dioxane. In a preferred embodiment of this invention, the solvent is THF.

The applicants found that 2-(5-benzyloxy-2-vinylphenoxy)-1-(4-methoxyphenyl)ethanone can be easily obtained by reacting 4-benzyloxy-2-hydroxybenzaldehyde with a mixture of methyl triphenyl phosphonium bromide and a second base, followed by reaction with 2-bromo-4'-methoxyacetophenone.

4-Benzyloxy-2-hydroxybenzaldehyde can be readily obtained by those skilled in the art with reference to, e.g., S. Ramadas et al. (2000), *Tetrahedron: Asymmetry*, 11:3375-3393; and V. Maslak et al. (2006), *J. Am. Chem. Soc.*, 128: 5887-5894.

The second base suitable for use in the synthesis of 2-(5-benzyloxy-2-vinylphenoxy)-1-(4-methoxyphenyl)ethanone includes, but is not limited to: t-BuOK, t-BuONa, n-BuLi, PhLi, t-BuLi, NaH, NaHMDS, KHMDS, $Et_3N$, and sodium methoxide. In a preferred embodiment of this invention, the second base is t-BuOK.

In a preferred embodiment of this invention, the first base and the second base are the same.

The synthesis of 2-(5-benzyloxy-2-vinylphenoxy)-1-(4-methoxyphenyl)ethanone may be carried out in the presence of an appropriate solvent, including, but not being limited to: THF, $Et_2O$, THP, DMF, DMSO, DME, and dioxane. In a preferred embodiment of this invention, the solvent is THF.

This invention will be further described by way of the following examples. One of ordinary skill in the art is familiar with many techniques and teachings allowing the modification of these examples and the examples noted throughout this disclosure that would also employ the basic, novel, or advantageous characteristics of the invention. Thus, the scope of this invention is not limited by the particular examples listed here or elsewhere.

EXAMPLES

7-Benzyloxy-3-(4-methoxyphenyl)-2H-1-benzopyran can be prepared according to the following reaction scheme and protocols. Referring to Scheme 1, 4-benzyloxy-2-hydroxybenzaldehyde (compound 1) was reacted with a mixture of methyl triphenyl phosphonium bromide (MTPPB) and potassium tert-butoxide (t-BuOK), followed by reaction with 2-bromo-4'-methoxyacetophenone to give 2-(5-benzyloxy-2-vinylphenoxy)-1-(4-methoxyphenyl)ethanone (compound 2a), which was subsequently reacted with a mixture of MTPPB and t-BuOK to give 4-benzyloxy-2-[2-(4-methoxyphenyl)allyloxy]-1-vinylbenzene (compound 2). Reaction of compound 2 with Grubbs' catalyst (II) gives 7-benzyloxy-3(4-methoxyphenyl)-2H-1-benzopyran (compound 3).

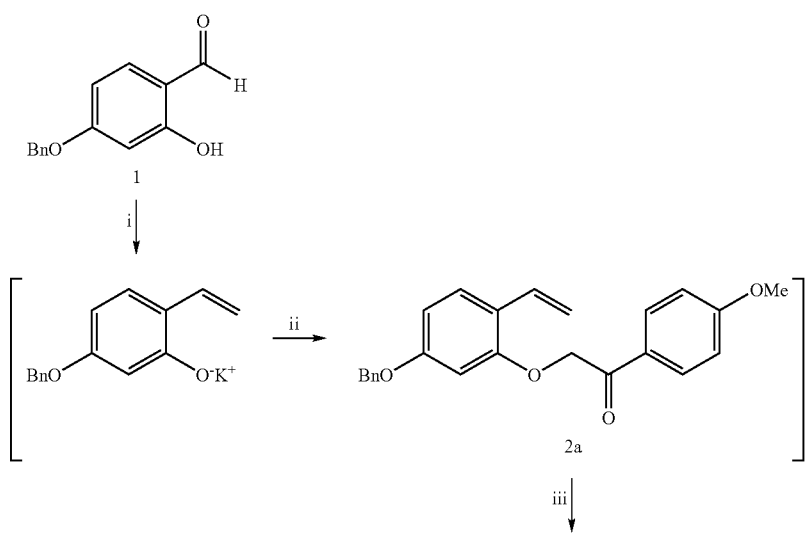

Scheme 1

-continued

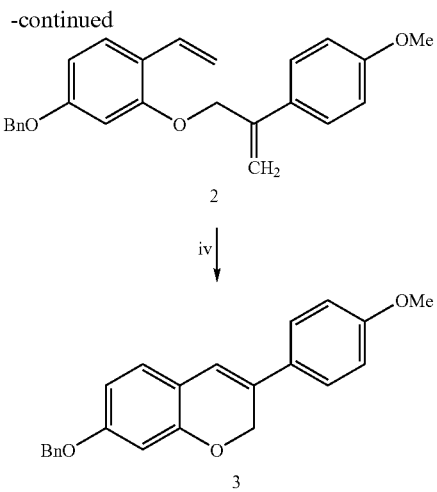

Reagents and Reaction Conditions:

i. MTPPB, t-BuOK, THF, 0° C., 2 hrs:

ii. 2-bromo-4'-methoxyacetophenone, reflux, 1 hr;

iii. MTPPB, t-BuOK, THF, 0° C., 2 hrs;

iv. Grubbs' catalyst (II), CH$_2$Cl$_2$, 40° C., 8 hrs.

General Procedures;

The general TLC was performed using pre-coated silica gel 60 F$_{254}$ plates (E. Merck Company) and detected using UV light at 254 nm.

The melting point of each of the compounds synthesized in the following examples was detected using an uncorrected Yanaco micro melting-point apparatus.

The column chromatography was performed using silica gel (sieve mesh 230-400 mm, manufactured by E. Merck Company) as the solid phase in combination with a suitable eluent for separation and purification.

$^1$H-NMR and $^{13}$C-NMR spectra were detected using a Varian Gemini-200 or Varian Unity plus 400 spectrometer. Chemical shifts are indicated in parts per million with respect to TMS.

IR spectra were measured on a Perkin Elmer system 2000 FT-IR spectrometer.

Elemental analyses were recorded on a Heraeus CHN—O Rapid analyzer.

Electron impact mass spectra (EI-MS) were recorded on a Chem/hp/middle spectrometer connected to a Hewlett Packard series II model gas-liquid chromatography.

High-resolution mass spectra (HRMS) were performed on a JEOL JMS SX/SX 102A instrument.

Ex. 1

Synthesis of 4-benzyloxy-2-[2-(4-methoxyphenyl)allyloxy]-1-vinylbenzene (compound 2)

A. Synthesis of 2-(5-benzyloxy-2-vinylphenoxy)-1-(4-methoxyphenyl)ethanone (compound 2a)

A suspension of methyl triphenyl phosphonium bromide (MTPPB, 16.90 g, 47.31 mmol) in anhydrous THF (50 mL) was cooled in an ice bath and added with potassium tert-butoxide (t-BuOK, 5.31 g, 47.32 mmol) in portions under nitrogen. After stirring at 0° C. for 15 min, a mixture of 4-benzyloxy-2-hydroxybenzaldehyde (1)(9.0 g, 39.43 mmol), t-BuOK (4.87 g, 43.40 mmol) and THF (50 mL) was added, and the resultant mixture was stirred at 0° C. for 2 hrs. Thereafter, the mixture was heated under reflux, and a solution of 2-bromo-4'-methoxyacetophenone (10.85 g, 47.36 mmol) in THF (30 mL) was added dropwise. After stirring under reflux for 1 hr (TLC monitoring), the mixture was quenched with a saturated NH$_4$Cl solution. After removal of most of the THF in vacuo, the resultant residue was extracted six times with EtOAc (50 mL). The organic layers were combined, washed with a saturated NaCl solution, and dried with anhydrous MgSO$_4$. After filtration, the filtrate was concentrated in vacua, followed by purification via silica gel column chromatography (ethyl acetate/n-hexane=1:15), thus giving the title compound 2a as a colorless crystal (11.81 g, 80% yield).

Defected Properties of the Title Compound:

M.p.: 93-94° C., R$_f$: 0.21 (ethyl acetate/n-hexane=1:9); IR (neat) v$_{max}$: 3063, 2930, 1691, 1601, 1574, 1501, 1453, 1419, 1311, 1261, 1236, 1169, 1122, 1026, 832 cm$^{-1}$; $^1$H-NMR (200 MHz, CDCl$_3$); δ 3.87 (s. 3H, OCH$_3$), 5.02 (s, 2H, OCH$_2$Ph), 5.17 (dd, J=11.2, 1.4 Hz, 1H, ArCH═CH$_a$H$_b$), 5.17 (s, 2H, OCH$_2$C═O), 5.68 (dd, J=17.8, 1.4 Hz, 1H, ArCH═CH$_a$H$_b$), 6.45 (d, J=2.6 Hz, 1H, ArH), 6.58 (dd, J=8.4, 2.6 Hz, 1H, ArH), 6.95 (d, J=9.0 Hz, 2H, ArH), 7.03 (dd, J=17.8, 11.2, 1H, ArCH═CH$_2$), 7.33-7.43 (m, 6H, ArH), 7.97 (d, J=9.0, 2H, ArH); $^{13}$C-NMR (50 MHz, CDCl$_3$): δ 55.5, 70.2, 71.3, 100.7, 107.0, 112.8, 114.0, 120.6, 127.5, 127.7, 128.0, 128.6, 130.5, 131.0, 136.7, 156.3, 159.5, 164.0, 192.6; EIMS (70 eV) m/z (relative intensity, %): 374 (M+, 40), 345 (11), 225 (27), 224 (17), 150 (20), 135 (99), 121 (17), 92 (11), 91 (100), 77 (14), 65 (14). Anal. calcd for C$_{24}$H$_{22}$O$_4$: C, 76.99; H, 5.92. found: C, 76.96; H, 5.90.

1B. Synthesis of 4-benzyloxy-2-[2-(4-methoxyphenyl)allyloxy]-1-vinylbenzene (compound 2)

A suspension of MTPPB (2.29 g, 6.41 mmol) in anhydrous THF (20 mL) was cooled in an ice bath and added with t-BuOK (0.72 g, 6.42 mmol) in portions under nitrogen. After stirring at 0° C. for 15 min, the suspension was added with compound 2a (2.0 g, 5.34 mmol) as obtained above. The resultant mixture was stirred at 0° C. for 2 hrs, followed by quenching with a saturated NH$_4$Cl solution. After removal of most of the THF in vacuo, the resultant residue was extracted six times with EtOAc (20 mL). The organic layers were combined, washed with a saturated NaCl solution, and dried with anhydrous MgSO$_4$. After filtration, the filtrate was concentrated in vacuo, followed by purification via silica gel column chromatography (ethyl acetate/n-hexane=1:15), thus giving the title compound 2 as a colorless liquid (1.89 g, 95% yield).

Detected Properties of the Title Compound:

R$_f$: 0.60 (ethyl acetate/n-hexane=1:9); IR (neat) $v_{max}$: 3033, 2932, 1606, 1512, 1501, 1251, 1175, 1029, 834 cm$^{-1}$; $^1$H-NMR (400 MHz, CDCl$_3$): δ 3.79 (s, 3H, OCH$_3$), 4.83 (s, 2H, OCH$_2$C=CH$_2$), 5.03 (s, 2H, OCH$_2$Ph), 5.08 (dd, J=11.2, 1.6 Hz, 1H, ArCH=CH$_a$H$_b$), 5.36 (d, J=1.2 Hz, 1H, OCH$_2$C=CH$_a$H$_b$), 5.51 (d, J=1.2 Hz, 1H, OCH$_2$C=CH$_a$H$_b$), 5.58 (dd, J=17.6, 1.6 Hz, 1H, ArCH=CH$_a$H$_b$), 6.56 (dd, J=8.4, 2.4 Hz, 1H, ArH), 6.58 (d, J=2.4 Hz, 1H, ArH), 6.87 (d, J=8.8 Hz, 2H, ArH), 6.93 (dd, J=17.6, 11.2, 1H, ArCH=CH$_2$), 7.29-7.42 (m, 6H, ArH), 7.39 (d, J=8.8, 2H, ArH); $^{13}$C-NMR (100 MHz, CDCl$_3$): δ 55.2, 70.1, 70.2, 100.6, 106.2, 112.3, 113.0, 113.8, 120.4, 127.10, 127.12, 127.5, 128.0, 128.6, 130.7, 131.0, 136.8, 142.1, 156.7, 159.4, 159.5; EIMS (70 eV) m/z (relative intensity, %): 372 (M$^+$, 13), 281 (24), 176 (13), 175 (100), 174 (83), 173 (76), 145 (26), 91 (40). HRMS calcd for C$_{25}$H$_{24}$O$_3$Na (M$^+$+Na): 395.1623. found: 395.1625.

Alternatively, the compound 2 can be obtained by reacting 4-benzyloxy-2-hydroxybenzaldehyde with a mixture of MTPPB and t-BuOK, followed by reaction with 2-bromo-4'-methoxyacetophenone, and the resultant mixture, instead of being subjected to purification to afford compound 2a, was continuously reacted with a mixture of MTPPB and t-BuOK in THF, giving a one pot yield of 74%.

Ex. 2

Synthesis of 7-benzyloxy-3-(4-methoxyphenyl)-2H-1-benzopyran (compound 3)

A solution of compound 2 as obtained in the above Example 1 (2.4 g, 6.44 mmol) in CH$_2$Cl$_2$ (210 mL) was stirred at 40° C. under nitrogen, followed by addition of Grubbs' catalyst (II)(0.27 g, 0.32 mmol)(Aldrich 569747-2G). The resultant mixture was stirred at 40° C. for 8 hrs, followed by concentration in vacuo. The resultant residue was purified via silica gel column chromatography (ethyl acetate/n-hexane=1:15) to give the title compound 3 as a colorless crystal (1.81 g, 82% yield).

Detected Properties of the Title Compound:

M.p.: 152-154° C. (lit: 154-155° C.); R$_f$: 0.32 (ethyl acetate/n-hexane=1:15); IR (KBr) $v_{max}$: 2951, 1610, 1512, 1256, 1169, 1007, 829 cm$^{-1}$; $^1$H-NMR (400 MHz, CDCl$_3$): δ 3.82 (s, 3H, OCH$_3$), 5.04 (s, 2H, OCH$_2$C$_5$H$_5$), 5.11 (d, J=1.2 Hz, 2H, H-2), 6.52 (d, J=2.4 Hz, 1H, H-8), 6.54 (dd, J=8.4, 2.4 Hz, 1H, H-6), 6.68 (br s, 1H, H-4), 6.91 (d, J=8.8 Hz, 2H, H-3', H-5'), 6.98 (d, J=8.4 Hz, 1H, H-5), 7.35 (d, J=8.8 Hz, 2H, H-2', H-6'), 7.32-7.44 (m, 5H, ArH); $^{13}$C-NMR (100 MHz, CDCl$_3$): δ 55.3, 67.3, 70.1, 102.4, 108.2, 114.1, 116.7, 118.0, 125.8, 127.4, 127.5, 128.0, 128.5, 128.6, 129.5, 136.8, 154.2, 159.2, 159.5; EIMS (70 eV) m/z (relative intensity, %) 345 ([M+1]$^+$, 20), 344 (M$^+$, 81), 254 (28), 253 (100), 226 (20), 225 (36), 91 (13). HRMS calcd for C$_{23}$H$_{20}$O$_3$Na (M$^+$+Na): 367.1310; found: 367.1311. Anal. calcd for C$_{23}$H$_{20}$O$_3$: C, 80.21; H, 5.85. found: C, 80.03; H, 5.85.

All patents and literature references cited in the present specification as well as the references described therein, are hereby incorporated by reference in their entirety. In case of conflict, the present description, including definitions, will prevail.

While the invention has been described in connection with specific embodiments thereof it will be understood that it is capable of further modifications and this application is intended to cover any variations, uses, or adaptations of the invention following, in general, the principles of the invention and including such departures from the present customary practice within the art to which the invention pertains and as may be applied to the essential features hereinbefore set forth, and as follows in the scope of the appended claims.

We claim:

1. A compound of formula (I):

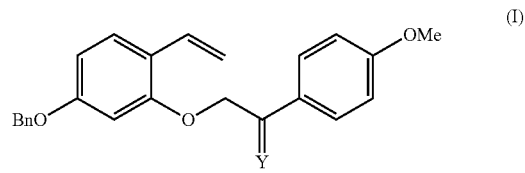

wherein:
Bn represents benzyl;
Me represents methyl; and
Y represents an oxygen atom or a CH$_2$ group.

2. A process for preparing 7-benzyloxy-3-(4-methoxyphenyl)-2H-1-benzopyran, comprising subjecting a compound of formula (I):

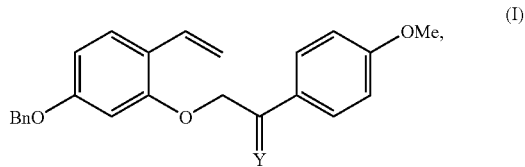

wherein Bn represents benzyl, Me represents methyl, and Y is a CH$_2$ group; to a ring closing metathesis reaction in the presence of a catalyst.

3. The process according to claim 2, wherein the catalyst is selected from the group consisting of: Grubbs' catalyst (II), Hoveyda-Grubbs' catalyst, and Grubbs' catalyst (I).

4. The process according to claim 2, wherein the ring closing metathesis reaction is carried out in the presence of a solvent selected from the group consisting of CH$_2$Cl$_2$, benzene, and toluene.

5. A process for preparing a compound of formula (I):

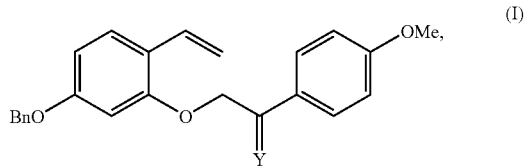

wherein Bn represents benzyl, Me represents methyl, and Y is a CH$_2$ group; the process comprising:

reacting 2-(5-benzyloxy-2-vinylphenoxy)-1-(4-methoxyphenyl)ethanone with a mixture of methyl triphenyl phosphonium bromide and a first base.

6. The process according to claim 5, wherein the first base is selected from the group consisting of: potassium tert-butoxide, sodium tert-butoxide, n-butyllithium, phenyllithium, tert-butyllithium, sodium hydride, sodium hexamethyldisilazide, potassium hexamethyldisilazide, triethylamine, and sodium methoxide.

7. The process according to claim 5, wherein the process is implemented in the presence of a solvent selected from the group consisting of tetrahydrofuran, diethyl ether, tetrahydropyran, N,N-dimethylformamide, dimethyl sulfoxide, dimethoxyethane, and dioxane.

8. The process according to claim 5, wherein 2-(5-benzyloxy-2-vinylphenoxy)-1-(4-methoxyphenyl)ethanone is prepared by reacting 4-benzyloxy-2-hydroxybenzaldehyde with methyl triphenyl phosphonium bromide and a second base, followed by reaction with 2-bromo-4'-methoxyacetophenone.

9. The process according to claim 8, wherein the second base is selected from the group consisting of: potassium tert-butoxide, sodium tert-butoxide, n-butyllithium, phenyllithium, tert-butyllithium, sodium hydride, sodium hexamethyldisilazide, potassium hexamethyldisilazide, triethylamine, and sodium methoxide.

10. The process according to claim 8, wherein preparation of 2-(5-benzyloxy-2-vinylphenoxy)-1-(4-methoxyphenyl)ethanone is implemented in the presence of a solvent selected from the group consisting of tetrahydrofuran, diethyl ether, tetrahydropyran, N,N-dimethylformamide, dimethyl sulfoxide, dimethoxyethane, and dioxane.

* * * * *